United States Patent [19]
Eberbach

[11] Patent Number: 5,275,610
[45] Date of Patent: Jan. 4, 1994

[54] SURGICAL RETRACTORS AND METHOD OF USE

[75] Inventor: Mark A. Eberbach, Tampa, Fla.

[73] Assignee: Cook Incorporated, Bloomington, Ind.

[21] Appl. No.: 18,333

[22] Filed: Feb. 12, 1993

Related U.S. Application Data

[63] Continuation of Ser. No. 699,358, May 13, 1991, abandoned.

[51] Int. Cl.$^5$ ............................................. A61M 29/00
[52] U.S. Cl. ...................................... 606/198; 604/105
[58] Field of Search ........................................ 604/104–; 606/127, 128, 191, 198

[56] References Cited

U.S. PATENT DOCUMENTS

| 698,447 | 4/1902 | Bush . | |
|---|---|---|---|
| 827,193 | 7/1906 | Thrash . | |
| 833,759 | 10/1906 | Sourwine | 604/105 |
| 862,712 | 8/1907 | Collins . | |
| 1,433,031 | 10/1922 | Pegaitaz . | |
| 2,586,553 | 2/1952 | Moscarello | 604/105 |
| 3,312,222 | 4/1967 | Dwyer . | |
| 3,495,586 | 2/1970 | Regenbogen | 604/105 |
| 3,517,128 | 6/1970 | Hines | 606/198 |
| 3,557,794 | 1/1971 | Van Patten | 606/198 |
| 3,799,172 | 3/1974 | Szpur . | |
| 4,580,568 | 4/1986 | Gianturco . | |
| 4,608,965 | 9/1986 | Anspach, Jr. et al. | 604/105 |
| 4,648,402 | 3/1987 | Santos | 606/198 |
| 4,654,028 | 3/1987 | Suma . | |
| 4,692,139 | 9/1987 | Stiles . | |
| 4,807,626 | 2/1989 | McGirr . | |
| 4,808,163 | 2/1989 | Laub . | |

FOREIGN PATENT DOCUMENTS

| 295717 | 12/1899 | France | 606/198 |
|---|---|---|---|
| 1169419 | 11/1969 | United Kingdom . | |

Primary Examiner—Stephen C. Pellegrino
Assistant Examiner—William W. Lewis
Attorney, Agent, or Firm—Richard J. Godlewski

[57] ABSTRACT

An improved laparoscopic medical retractor for separating body parts during a surgical procedure to thereby create or maintain a surgical cavity. The retractor comprises an interior rod having a distal end and a proximal end and an exterior tube positioned to receive the central rod, the exterior tube having a distal end and a proximal end. A plurality of straps having their distal ends are coupled to the distal end of the interior rod and have their proximal ends coupled to the distal end of the exterior tube. The straps are flexible whereby movement of the distal end of the exterior tube distally toward the distal end of the interior rod will cause the straps to assume a generally spherical configuration, the total diameter of the retracted device being less than 1.5 centimeters. Coupling means secure the interior rod and exterior tube against relative axial movement with respect to each other so that a surgeon may move the expanded retractor to enlarge a surgical cavity in which it is located.

13 Claims, 7 Drawing Sheets

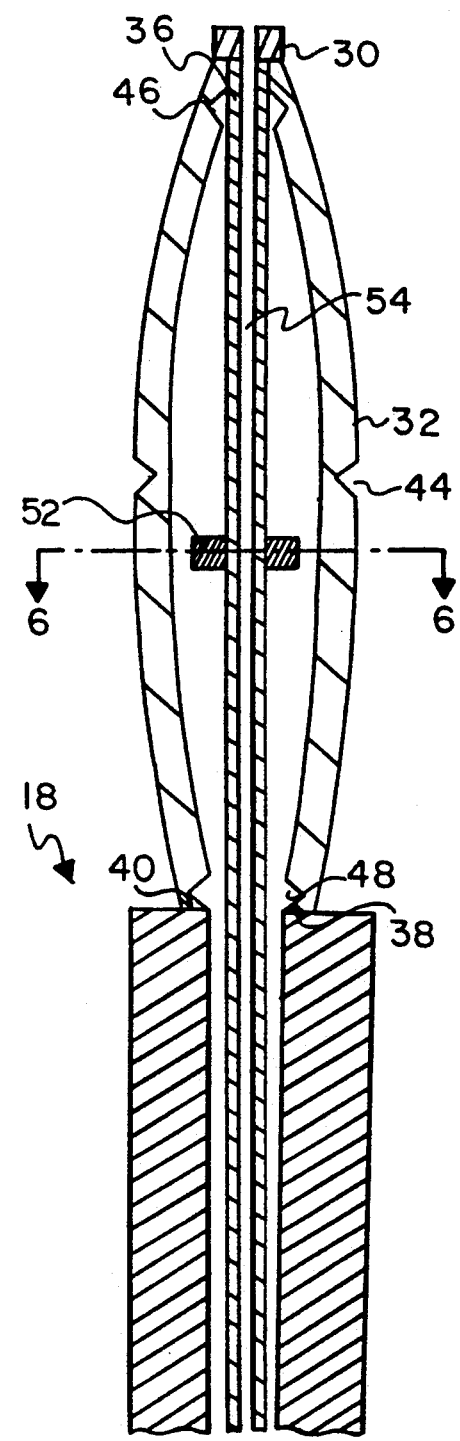
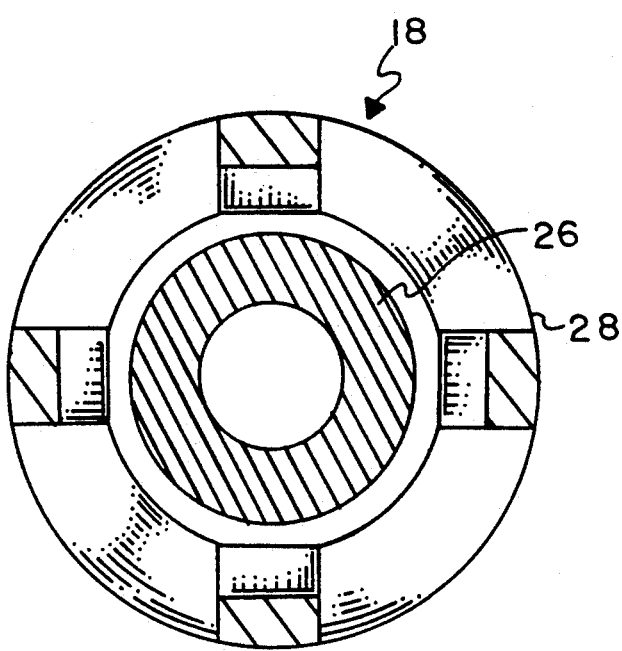
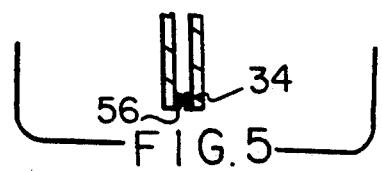

SURGICAL RETRACTORS AND METHOD OF USE

This is a continuation of copending application Ser. No. 07/699,358 filed on May 13, 1991, now abandoned.

BACKGROUND OF THE INVENTION

1. Summary of the Invention

This invention relates to medical retractors and, more particularly, to laparoscopic devices for effecting separation of body parts adjacent to a surgical cavity.

2. Summary of the Background Art

Many common ailments of humans require surgical intervention to effect a cure. Until recently, most surgical procedures required large incisions. Recent application of laparoscopic techniques has permitted surgery to be performed with much smaller incisions. With these techniques, exposure of the operative sight may be limited. As such, devices to separate or retract tissues would facilitate the operative procedure. One example where increased exposure of the operative sight would be of benefit is the repair of an inguinal hernia via a laparoscopic approach.

According to the disclosure of my co-pending patent application, U.S. patent application Ser. No. 07/595,956 filed Oct. 11, 1990, laparoscopic mechanisms are disclosed for the repair of hernias from interior of the abdominal wall. According to the present invention, however, an puncture type incision is made through the abdominal wall including layers of skin, fat and muscle but not through the peritoneum. The peritoneum layer and the layers of the abdominal wall are then separated to form a surgical cavity. Laparoscopic techniques are then employed for the repair of the hernia. In such a procedure, however, retractor devices are helpful to retract, separate, and hold the peritoneum and the other abdominal layers to create and maintain a surgical cavity in which the surgeon may effect the laparoscopic surgical procedures for the repair of the hernia. Such laparoscopic procedures are described in my aforementioned application, the subject matter of which is incorporated herein by reference.

Various techniques and devices are employed commercially or are disclosed in the patent literature for retracting or manipulating various body parts during surgical procedures. Such procedures include devices and techniques for retracting body parts adjacent to a surgical cavity. Note, for example, U.S. Pat. Nos. 4,580,568; 4,654,028; 4,692,139 and 4,808,163 which relate to expansion devices for insertion into veins. In addition, U.S. Pat. Nos. 3,799,172 and 4,807,626 as well as U.K. Patent Number 1169419 relate to expander devices for urinary systems. In addition, U.S. Pat. Nos. 698,447; 862,712; 1,433,031 and 3,312,222 disclose expander devices for vaginal uses. Lastly, U.S. Pat. No. 3,517,128 relates to a surgical expander and dilator for a relatively large organ such as the stomach, bladder or colon.

As illustrated by the great number of prior patents as well as other commercial devices and techniques, efforts are continuously being made in an attempt to improve devices for manipulating body parts for one purpose or another. Such efforts are being made to render such devices more efficient, reliable, inexpensive and convenient to use. None of these previous efforts, however, provides the benefits attendant with the present invention. Additionally, the prior patented and commercial devices and techniques do not suggest the present inventive combination of method steps and component elements arranged and configured as disclosed and claimed herein.

The present invention achieves its intended purposes, objects and advantages through a new, useful and unobvious combination of method steps and component elements, with the use of a minimum number of functioning parts, at a reasonable cost to manufacture, and by employing only readily available materials.

Accordingly, it is an object of the present invention to provide an improved laparoscopic surgical retractor for separating body parts during a surgical procedure to thereby create or maintain a surgical cavity. The retractor comprises an interior rod having a distal end and a proximal end and an exterior tube positioned to receive the central rod, the exterior tube having a distal end and a proximal end. A plurality of straps having their distal ends coupled to the distal end of the interior rod and have their proximal ends coupled to the distal end of the exterior tube. The straps are flexible whereby movement of the distal end of the interior rod proximally toward the distal end of the exterior tube will cause the straps to assume a generally spherical configuration, the total diameter of the retracted non-expanded device being less than 1.5 centimeters. Coupling means secure the interior rod and exterior tube against relative axial movement with respect to each other so that a surgeon may move the expanded retractor to enlarge a surgical cavity in which it is located.

It is a further object of the present invention to employ surgical retractors to create or maintain surgical cavities during laparoscopic procedures.

It is a further object of the invention to effect separation of body parts at a surgical cavity by laparoscopic retractors.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with specific embodiments shown in the attached drawings. For the purpose of summarizing this invention, the invention may be incorporated into an improved laparoscopic medical retractor for separating body parts during a surgical procedure to thereby create or maintain a surgical cavity. The retractor comprises an interior rod having a distal end and a proximal end and an exterior tube positioned to receive the central rod, the exterior tube having a distal end and a proximal end. A plurality of straps have their distal ends coupled to the distal end of the interior rod and have their proximal ends coupled to the distal end of the exterior tube. The straps are flexible whereby movement of the distal end of the interior rod proximally toward the distal end of the exterior tube will cause the straps to assume a generally spherical configuration, the total diameter of the non-expanded device being less than 1.5 centimeters. length of the straps constitutes between about 33 and 50 percent of the length of the device. Coupling means secure the interior rod and exterior tube against relative axial movement with respect to each other so that a surgeon may move the expanded retractor to enlarge a surgical cavity in which it is located.

The length of the straps constitutes between about 33 and 50 percent of the length of the device. The straps may be fabricated of plastic or metal. The straps have pivot points adjacent to their ends. The straps may have pivot points adjacent to their middles. The pivot points may be recesses or hinges. The straps may be fabricated of metal with a bowed cross sectional configuration. The interior rod may be hollow with a central axial passageway to thereby constitute a laparoscopic channel with the passageway including a self-sealing diaphragm. The straps may be two in number and further including fabric fabric coupling the straps for forming a planar retractor when the straps are expanded. The straps are formed with an interior component and an exterior component bonded along their lengths with the exterior components being more rigid, less flexible, than the interior components.

The invention may also be incorporated into an improved laparoscopic medical retractor for separating body parts during a surgical procedure to thereby create a surgical cavity. The retractor comprises an interior rod having a distal end and a proximal end and an exterior tube positioned to receive the central rod, the exterior tube having a distal end and a proximal end. A plurality of straps have their distal ends coupled to the distal end of the interior rod and have their proximal ends coupled to the distal end of the exterior tube. The straps are flexible whereby movement of the distal end of the interior rod proximally toward the distal end of the exterior tube will cause the straps to assume a generally spherical configuration, the total diameter of the non-expanded device being less than 1.5 centimeters, and the length of the straps constituting between about 33 and 50 percent of the length of the device. A supplemental tube receives the exterior tube with axial recesses on the interior surface adapted to receive the straps. Coupling means secure the interior rod and exterior tube against relative axial movement with respect to each other so that a surgeon may move the expanded retractor radially to enlarge or maintain a surgical cavity in which it is located.

The apparatus further includes coupling means to join the exterior tube with respect to the interior rod. The apparatus further includes additional coupling means to join the supplemental tube with respect to the exterior tube.

The invention may also be incorporated into a method of increasing a surgical cavity by the retraction of adjacent body parts comprising the steps of providing an interior rod having a distal end and a proximal end; providing an exterior tube positioned to receive the central rod, the exterior tube having a distal end and a proximal end; providing a plurality of straps having distal ends coupled to the distal end of the interior rod and having proximal ends coupled adjacent to the distal end of the exterior tube; positioning the straps at the distal ends of the rod and tube through a laparoscopic channel or port and into the surgical cavity; and moving the rod proximally to move the straps into a configuration for contacting and retracting the adjacent body parts. The method further includes providing a supplemental tube receiving the straps and the interior rod and exterior tube with a portion of the straps located within the exterior tube during the moving of the rod to thereby determine the functional size and configuration of the straps.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other methods and structures for carrying out the same purposes of the present invention. It should also be realized by those skilled in the art that such equivalent methods and structures do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 5 is a sectional view of the retractor device of FIGS. 2, 3 and 4 taken along line 5—5 of FIG. 2.

FIG. 6 is a sectional view of the retractor device of FIGS. 2 through 5 taken along line 6—6 of FIG. 5.

Similar reference numerals refer to similar parts throughout the various figures.

DETAILED DESCRIPTION OF THE INVENTION

Shown in the various Figures are three retractors representing three embodiments of the present invention. FIGS. 2 through 15 illustrate the three embodiments of the present invention in various positions for being used during a surgical procedure.

Figure 1:
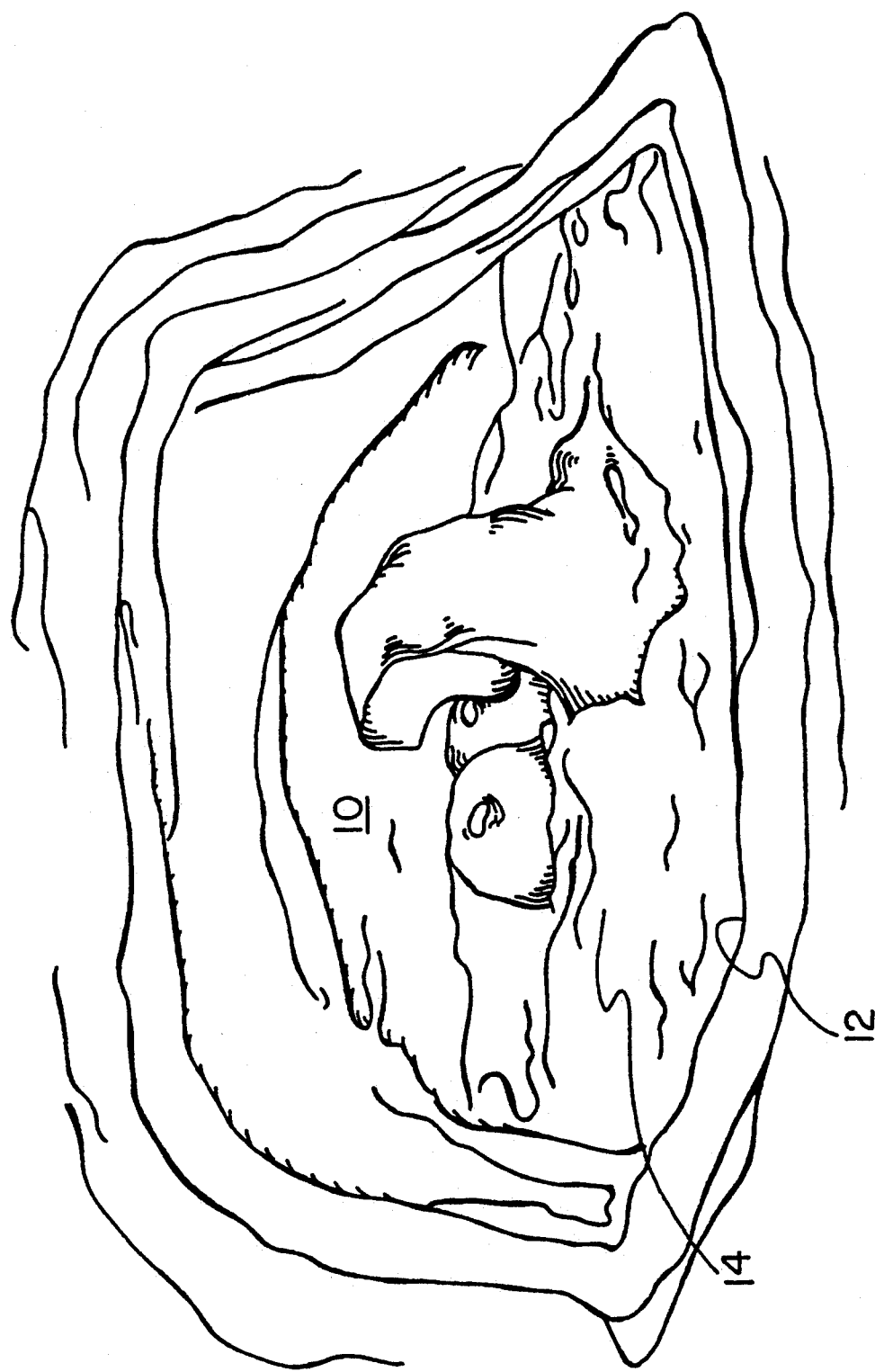
FIG. 1 shows layers of the abdominal wall adjacent to the location where hernias normally occur and where the surgical retractors of the present invention may be utilized.
Figure 2:
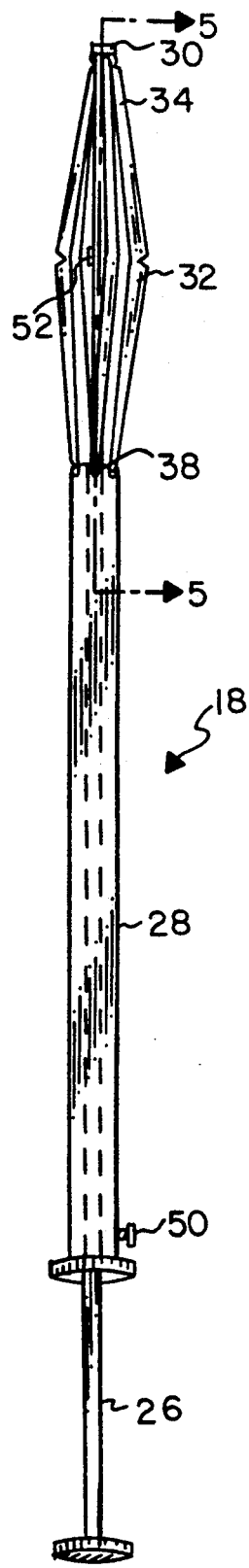
FIGS. 2, 3 and 4 are plan views of the retractor device constructed in accordance with the primary embodiment of the invention, the device being shown in a retracted, partially expanded and fully expanded orientation.

FIG. 1 shows a surgical cavity 10 and various layers 12 of the abdominal wall including skin, fat and muscle. Such layers 12 are illustrated as being separated from the uncut peritoneum layer 14. This space formed between the peritoneum and adjacent layers is the surgical cavity 10 where the retractor devices of the present invention are utilized. In each embodiment, a retractor device is used to pull or push a body part, retract or hold it, and thereby expand a space to render it of sufficient size and shape for effecting an appropriate surgical procedure such as the repair of a hernia.

In FIGS. 2 through 6 the retractor device 18 is adapted to pull the layers 12 of muscle, fat and skin away from the peritoneum layer 14 to thereby form and maintain a surgical cavity. An alternate embodiment is shown in FIGS. 7 through 11, wherein the retractor device 20 is used to push the peritoneum layer 14 away from the layers 12 of muscle, fat and skin, again for forming and maintaining the surgical cavity. Lastly, FIGS. 12 through 15 show a retractor device 22 for the same surgical cavity 10 as in the prior Figures. The retractor device 22 of the third embodiment is for the same purposes as the retractor device of FIGS. 7-11. In all embodiments, one layer is retracted from another layer for cavity expansion purposes. It should be understood that the devices may be used interchangeably to the extent that any one, two or more of such devices may be used in combination for the purposes as described herein. Similarly, any two or more of the same device may be used during a single surgical procedure.

FIRST EMBODIMENT

With more particular reference to FIGS. 2 through 6, there is shown a central rod 26 located within an external tube 28. Secured to the distal end 30 of the interior rod are a plurality of straps 32. Such straps are secured at their distal ends 34 to the distal end 36 of the interior rod and, at their proximal ends 38 to the distal ends 40 of the exterior tube 28. When the interior rod 26 and exterior tube 28 are moved with respect to each other so that their distal ends are separated a maximum distance, such maximal distance will correspond to the linear length of the straps 32. In such orientation, the device consisting of rod, tube and straps is at a minimum diameter. The minimum diameter is intended to be such as to fit within a sleeve or port located through an opening in the patient upon which laparoscopic surgery is to be performed. A port or sleeve is normally about 6 centimeters in length, with an inside diameter of between 5 millimeters and 1.5 centimeters. The exterior diameter of the device as described above and in the subsequent embodiments is sized to fit within a standard sleeve, less than 1.5 centimeters, normally about 1.0 centimeters.

Figure 3:
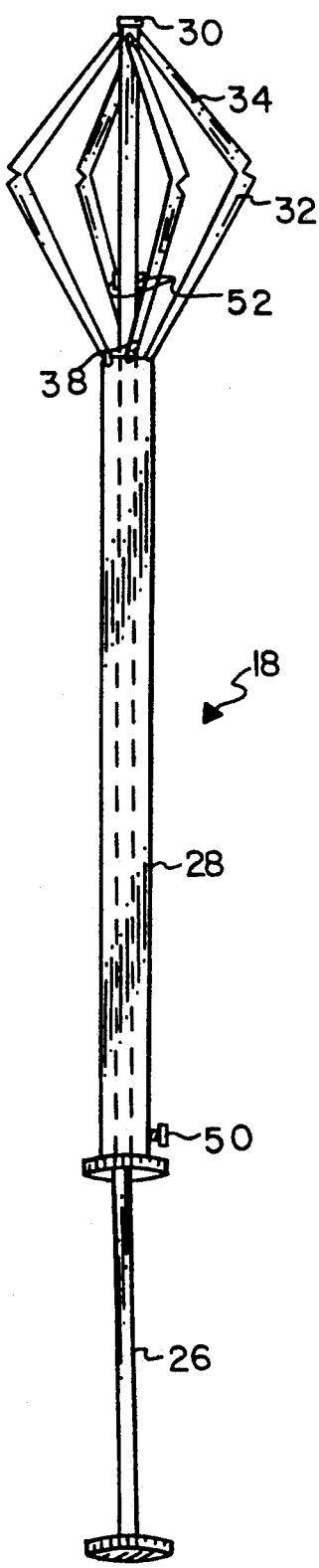
Figure 4:
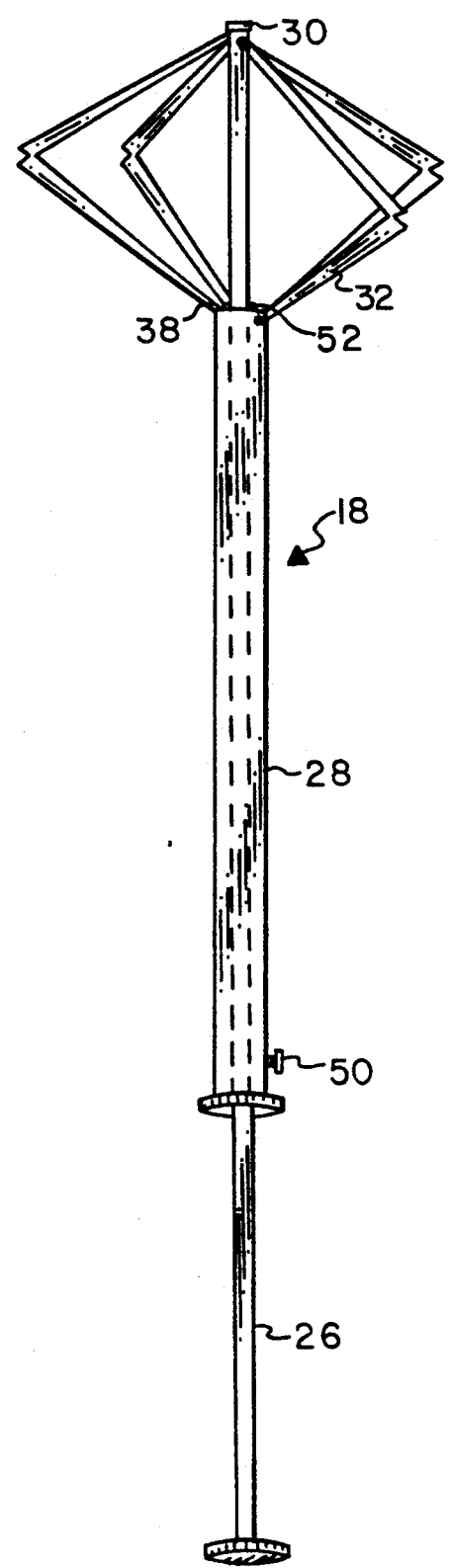
Figure 7:
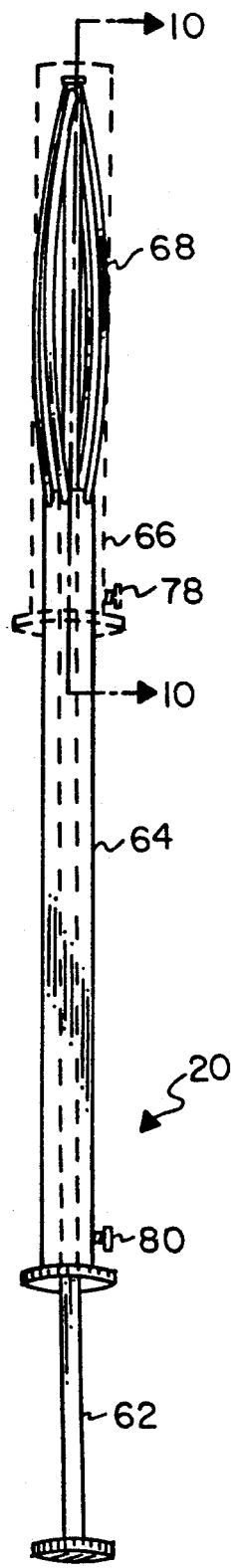
FIGS. 7, 8 and 9 are plan views of the retractor device constructed in accordance with the second embodiment of the invention, the device being shown in a retracted, partially expanded and fully expanded orientation.

Each of the straps 32 is adapted to be bendable about a midpoint to the various configurations as shown in FIGS. 4 through 6. In the preferred embodiment, each strap is bendable adjacent to its proximal end, its distal end, and at a central point along its length. Such areas of intending bending are insured by recesses 44 transverse to the axes of the straps to thereby allow the straps to move between their contracted and expanded positions. Additional notches 46 and 48 at the ends of the straps further facilitate movement of the straps between the open and closed orientations. Compare FIGS. 2 and 4. FIG. 3 illustrates an intermediate orientation.

When located within the surgical cavity 10 and in the expanded, operative position, a pulling motion by the surgeon from the proximal end outside the patient will effect pulling of the layers 12 of the abdominal wall away from the adjacent peritoneum layer 14 to enlarge and maintain the surgical cavity 10 for the convenient performing of laparoscopic surgery. A set screw 50 extending through a threaded aperture at the proximal end of tube 28 is used to abut rod 26 for releasably coupling the rod and tube. A collar 52 on the interior rod acts as an abutment surface for the distal end of the exterior rod to limit movement from the retracted position. The entire device is preferably between about 18 and 24 centimeters in length when in the retracted orientation.

The interior rod is preferably hollow with an axial passageway 54 so that it may constitute an additional laparoscopic channel. To this end, the passageway is fitted with a sealing diaphragm 56 in the form of an elastomeric member with a central aperture to receive the additional laparoscopic instruments while maintaining a sealing relationship between interior and exterior of the patient.

Each strap is preferably between about 6 and 12 centimeters in length and rectangular in cross-section. The straps 32 thus constitute about 33 to 50 percent of the length of the device. Four such straps are shown in the preferred embodiment. It should be realized, however, that any number of similar straps could be so utilized with the straps being symmetrically located around the circumference of the central rod and exterior tube.

Although plastic straps and weakened lines for bend points are shown in the preferred embodiment of FIGS. 2-6, it should be understood that flexible strands or flat straps could readily be utilized. Surgical steel is also an acceptable alternate material. The bend points could be formed by hinges at the ends of the strap where they couple with the rod and tube and intermediate thereof.

SECOND EMBODIMENT

The second embodiment of the invention is most readily seen in FIGS. 7 through 11. In this embodiment, an interior rod 62 is utilized in combination with an exterior tube 64. In addition, an exterior supplemental tube 66, over the exterior tube, is also utilized. The rod 62 and the plurality of straps 68, as in the first embodiment, are coupled at their distal and proximal ends to the distal end of the central rod and the distal end of the exterior tube, respectively. In this embodiment, the straps are fabricated preferably of a surgical steel material, about 6-12 centimeters in length, 0.2 centimeters in thickness. The straps 68 are formed with a slight curve in their cross sectional configuration. This tends to return the straps to their linear configuration after being bent or while being stored. A third or exterior supplemental tube 66 is located surrounding the central rod 62 and exterior tube 64 for receiving such components including the straps 68.

The interior surface of the exterior supplemental tube 66 is provided with a plurality of similarly sized and equally spaced longitudinal recesses 74 along its length. Such recesses correspond in size and number to the straps 68 utilized, four in the preferred embodiment. As in the first embodiment, a larger or smaller number could readily be utilized. The recesses 74 guide the movement of the straps 68 and provide torsional stability to the device 72 during operation and use. The entire device is between about 18 and 24 centimeters in length when in the retracted orientation. Each strap is between about 6 and 12 centimeters in length and thus constitutes between about 33 and 50 percent of the device.

In operation and use, the exterior tube 64 and interior rod 62 are pushed forward from the supplemental tube 66 so as to move into the space between the peritoneum layer 14 and other layers 12. When fully extended as in FIG. 9, the supplemental tube and interior rod are held by the surgeon and then the interior rod 62 is pulled rearwardly with respect to the exterior rod 64. Due to the reducing of length between the distal end of the interior rod and exterior tube, this will reshape the straps 68 from their linear orientation to a generally spherical orientation. When fully extended in the FIG. 9 orientation, opposed straps will assume an oval orientation with the shorter dimension axially with respect to the tubes. All three proximal ends of the rod and tubes will then be fixed with respect to each other as by set screws 78 and 80 coupling the supplemental tube 66 to the exterior tube 64 and the exterior tube 64 to the interior rod 62. A surgeon may then push the device forwardly to push the peritoneum layer 14 away from the layers 12 of muscle, fat and skin for enlarging the surgical cavity 10.

Figure 8:
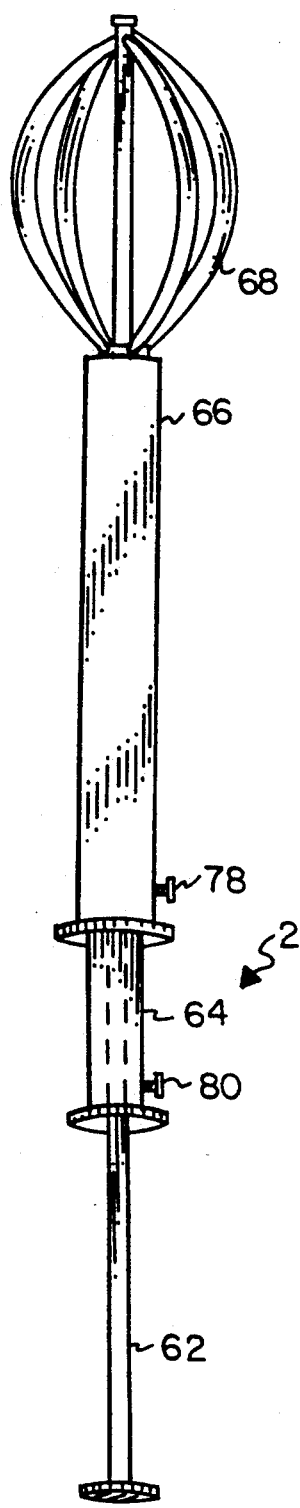
Figure 9:
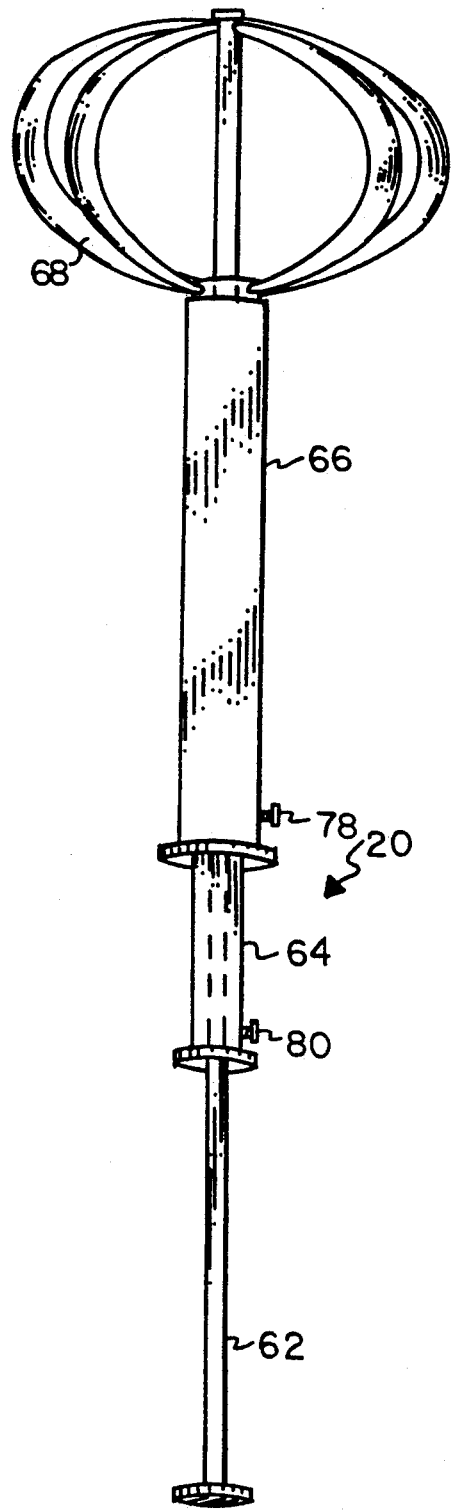
Figure 11:
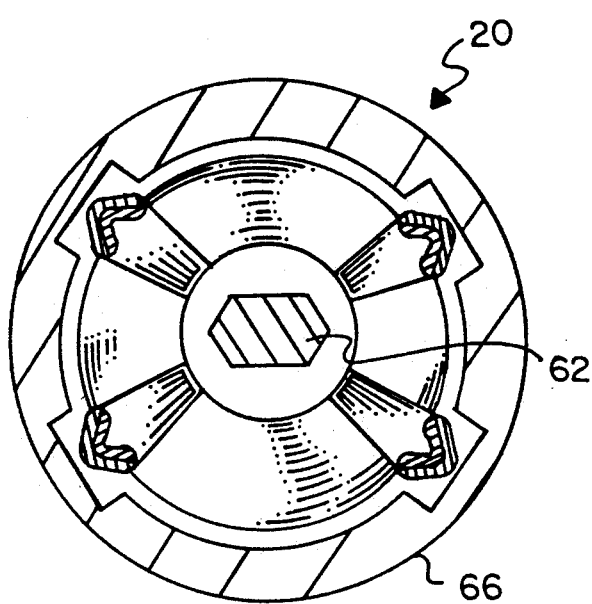
FIG. 11 is a sectional view of the retractor device of FIGS. 7 through 10 taken along line 11—11 of FIG. 10.
Figure 10:
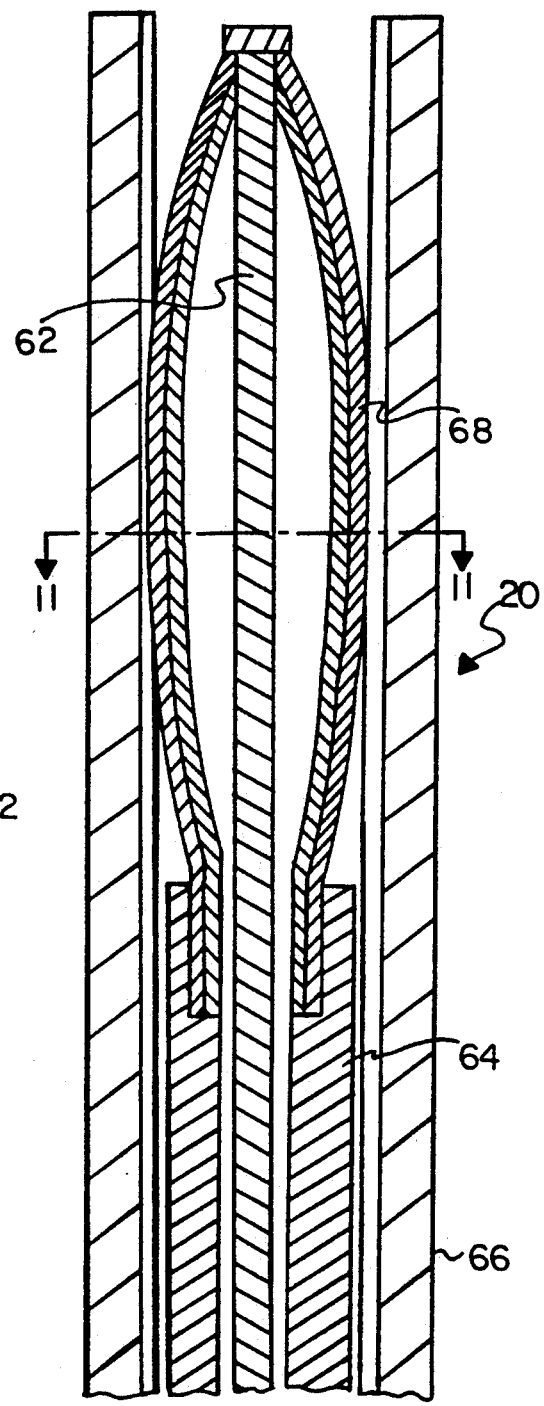
FIG. 10 is a sectional view of the retractor device of FIGS. 7, 8 and 9 taken along line 10—10 of FIG. 7.
Figure 12:
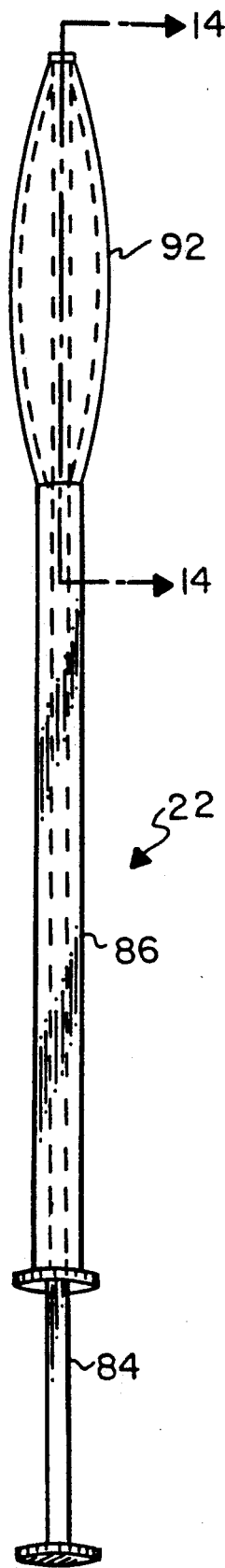
FIGS. 12 and 13 are plan views of the retractor device constructed in accordance with the third embodiment of the invention, the device being shown in a retracted and fully expanded orientation.
Figure 13:
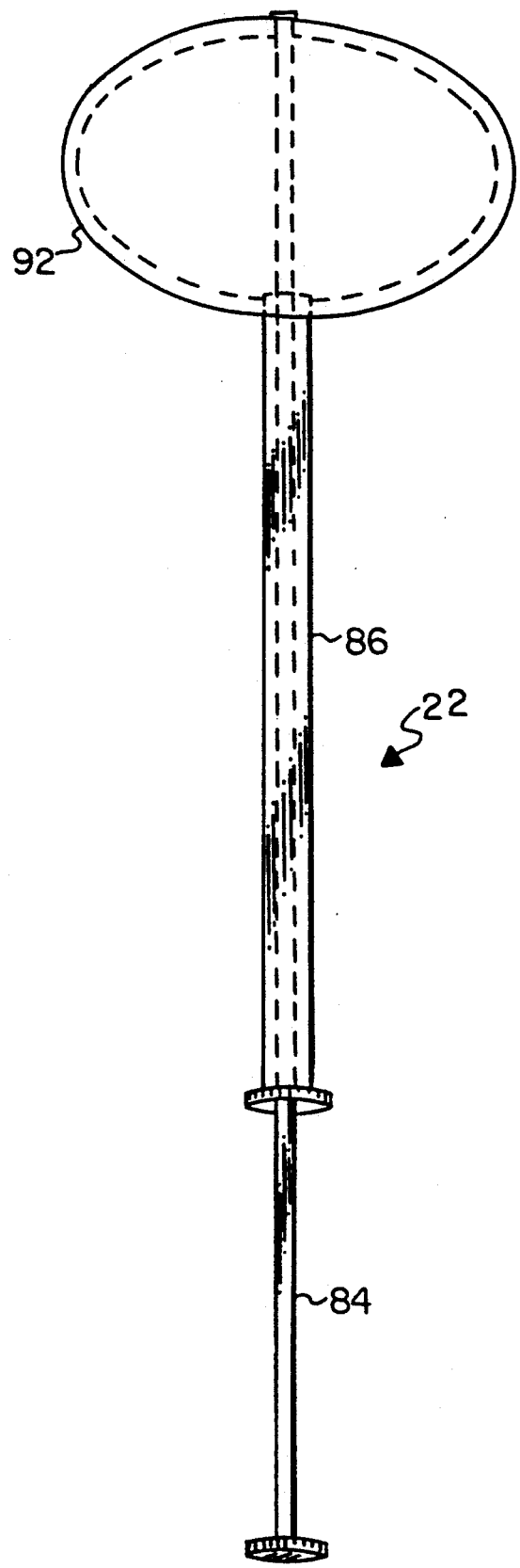
Figure 15:
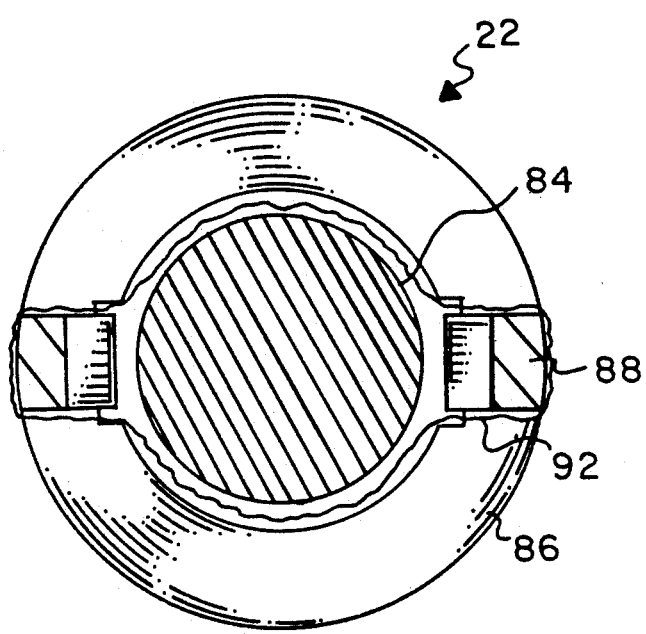
FIG. 15 is a sectional view of the retractor device of FIGS. 12 through 14 taken along line 15—15 of FIG. 14.
Figure 14:
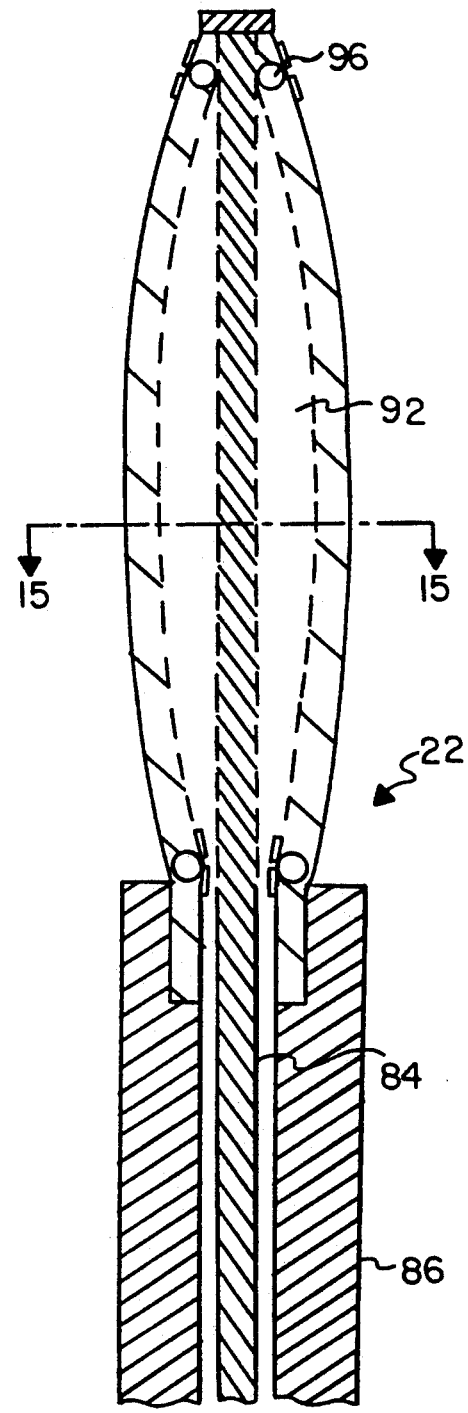
FIG. 14 is a sectional view of the retractor device of FIGS. 12 and 13 taken along line 14—14 of FIG. 12.

It should be understood that when a smaller sphere is desired for acting upon a smaller surgical cavity, the exterior tube 64 and interior rod 62 are pushed forwardly from the exterior supplemental tube 66 to a lesser extent thereby allowing only a portion of the straps 68 to be utilized in forming the sphere. Note the FIG. 8 showing.

In this second embodiment, the central rod 62 is preferably formed as a solid rod, not hollow. This is for added torsional stability. Torsional stability is also increased by coupling the proximal strap ends in axial recesses, inwardly from the distal end of the exterior tube. Further, in this second embodiment, the straps are shown as unitary devices of surgical spring steel. As in the first embodiment, other materials such as plastics could be utilized. Also, no bend points need be provided since various sized spheres may be formed.

THIRD EMBODIMENT

The final embodiment is shown in FIGS. 12 through 15. This third embodiment is similar to the prior two embodiments in that it utilizes a central rod 84, exterior tube 86 with straps 88 between the central rod and exterior tube. In the third embodiment, only two such straps are utilized. They are located on diametrically opposed sections of the device 22. In addition to the two straps, a fabric layer 92 is utilized. The fabric layer is attached along its lengths to the length of the straps 88 as by stitching, adhesion or the like. The fabric is a flexible material, preferably of an open mesh configuration. In addition, the fabric may be cut centrally along its length and attached to the exterior rod. In the alternative, it could be of a one piece configuration attached only along its edges to the straps.

In this embodiment, the pivot points are formed as hinges 96. The distal hinges couple the straps and interior rod. The proximal hinges couple the straps and exterior tube. As in the other embodiments, other types of pivot points could be utilized.

The entire device is of a size essentially the same as in the second embodiment, being between about 18 and 24 centimeters in length when in the retracted orientation. Each strap is between about 6 and 12 centimeters in length and thus constitutes between about 33 and 50 percent of the device.

In the second embodiment, the straps are formed as a laminate of two dissimilar materials, metal or plastic, bonded along their lengths, a bi-laminar construction. Such is not so in the first and third embodiments. In the second embodiments, the radially exterior strap component is formed of a more rigid material than the radially interior strap component. In this manner the outward bowing of the straps during expanding will provide a tension force resisting the bowing for thereby providing stability to the bowed straps. Each strap thereby constitutes a tension band. The use of the laminar construction is not required in this second embodiment where the use of straps are of a thicker configuration since the differences in curvature of the exposed surfaces will function as a tension band. In the third embodiment there is no need for bi-laminar construction since the cloth will provide the tension force resisiting the bowing. In the first embodiment, there is no bowing, hence, there is no need for the bi-laminar construction.

In operation and use, the third embodiment is intended to be utilized only with the straps, central rod, and fabric fully extended to form an oval shaped surface. An abutment collar to limit movement of the parts may be eliminated since the stretched fabric acts to limit relative movement between the rod and tube. Such surface may contact any surface, i.e., muscle, peritoneum, bowel, etc. to expand the surgical cavity for exposure.

The lengths of the various disclosed embodiments vary from 18 to 24 centimeters while the straps vary from 6 to 12 centimeters which consequently constitutes from 33 to 50 percent of the device.

METHOD

The method of using the present invention involves increasing a surgical cavity by the retraction of adjacent body parts through the use of the apparatus as described above. The method comprises the step of first providing an interior rod having a distal end and a proximal end. The method further includes the step of providing an exterior tube positioned to receive the central rod. As described in the foregoing, the exterior tube has a distal end and a proximal end. The method further includes the step of providing a plurality of straps having distal ends coupled to the distal end of the interior rod and having proximal ends coupled adjacent to the distal end of the exterior tube. After the providing of the components of the apparatus as described above, the method includes the step of positioning the straps at the distal ends of the rod and tube, between about 6 and 12 centimeters in length, through a sleeve or port and into the surgical cavity where the retraction is to take place. The central part of the apparatus, about 6 centimeters, is located with a port. The proximal end of the apparatus, normally about 6 centimeters or greater, is located exterior of the post and patient. Lastly, the method includes the step of moving the rod proximally while the tube is fixedly positioned to thereby move the straps into an expanded configuration. When in such expanded configuration, the straps may be used for contacting and retracting the adjacent body parts either through pushing or pulling.

The method may further include the step of providing a supplemental tube receiving the straps and the interior rod and exterior tube. A portion of the straps is located within the exterior tube and a portion of the straps is located distally thereof during the moving of the rod. The extent of the straps exterior of the tube thereby determines the size and configuration of the straps.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,
What is claimed is:

1. A laparoscopic medical retractor for separating body parts during a surgical procedure to thereby create or maintain a surgical cavity comprising:
   an interior rod having a distal end and a proximal end;
   an exterior tube positioned to receive the interior rod, the exterior tube having a distal end and a proximal end;
   a plurality of straps having their distal ends coupled to the distal end of the interior rod and having their proximal ends coupled in association with the distal end of the exterior tube, the straps having recessed pivot points adjacent to their middles and ends, the straps being flexible whereby movement of the distal end of the interior rod proximally toward the distal end of the exterior tube will cause the straps to assume a generally spherical configuration, the total diameter of the retracted device being less than 1.5 centimeters; and
   coupling means to secure the interior rod and exterior tube against relative axial movement with respect to each other so that a surgeon may move the expanded retractor to enlarge a surgical cavity in which it is located.

2. A laparoscopic medical retractor for separating body parts during a surgical procedure to thereby create or maintain a surgical cavity comprising:
   an interior rod having a distal end and a proximal end;
   an exterior tube positioned to receive the interior rod, the exterior tube having a distal end and a proximal end;
   a plurality of straps having their distal ends coupled to the distal end of the interior rod and having their proximal ends coupled in association with the distal end of the exterior tube, the straps being flexible whereby movement of the distal end of the interior rod proximally toward the distal end of the exterior tube will cause the straps to assume a generally planar configuration, the straps being two in number and further including fabric coupling the straps for forming an essentially planar retractor when the straps are expanded, the total diameter of the retracted device being less than 1.5 centimeters; and
   coupling means to secure the interior rod and exterior tube against relative axial movement with respect to each other so that a surgeon may move the expanded retractor to enlarge a surgical cavity in which it is located.

3. A laparoscopic medical retractor for separating body parts during a surgical procedure to thereby create or maintain a surgical cavity comprising:
   an interior rod having a distal end and a proximal end;
   an exterior tube positioned to receive the interior rod, the exterior tube having a distal end and a proximal end;
   a plurality of straps having their distal ends coupled to the distal end of the interior rod and having their proximal ends coupled in association with the distal end of the exterior tube, the straps being formed with an interior component and exterior component bonded along their lengths, the straps being flexible whereby movement of the distal end of the interior rod proximally toward the distal end of the exterior tube will cause the straps to assume a generally spherical configuration, the total diameter of the retracted device being less than 1.5 centimeters; and
   coupling means to secure the interior rod and exterior tube against relative axial movement with respect to each other so that a surgeon may move the expanded retractor to enlarge a surgical cavity in which it is located.

4. The apparatus as set forth in claim 3 wherein the exterior component of each strap is more rigid than the interior component.

5. A laparoscopic medical retractor for separating body parts during a surgical procedure to thereby create a surgical cavity comprising:
   an interior rod having a distal end and a proximal end;
   an exterior tube positioned to receive the interior rod, the exterior tube having a distal end and a proximal end;
   a plurality of elongated members having their distal ends coupled adjacent to the distal end of the interior rod and having their proximal ends coupled adjacent to the distal end of the exterior tube, each elongated member having a plurality of hinge points to facilitate lateral movement whereby axial movement of the distal end of the interior rod axially with respect to the distal end of the exterior tube will cause the elongated members to assume an expanded planar configuration, with all of the elongated members located in a common plane with the axes of the interior rod and external tube, the total diameter of the retracted unexpanded device being less than 1.5 centimeters; and
   coupling means to secure the interior rod and exterior tube against relative axial movement with respect to each other so that a surgeon may move the expanded retractor laterally to enlarge or maintain a surgical cavity in which it is located.

6. The retractor as set forth in claim 5 and further including a supplemental tube receiving the retractor.

7. A laparoscopic medical retractor for separating body parts during a surgical procedure to thereby create a surgical cavity comprising:
   an interior rod having a distal end and a proximal end;
   an exterior tube positioned to receive the interior rod, the exterior tube having a distal end and a proximal end;
   a plurality of elongated members having their distal ends coupled adjacent to the distal end of the interior rod and having their proximal ends coupled adjacent to the distal end of the exterior tube, each elongated member having a plurality of hinge points to facilitate lateral movement whereby axial movement of the distal end of the interior rod axially with respect to the distal end of the exterior tube will cause the elongated members to assume an expanded planar configuration, with all of the elongated members located in a common plane with the axes of the interior rod and external tube, the total diameter of the retracted unexpanded device being less than 1.5 centimeters;

coupling means to secure the interior rod and exterior tube against relative axial movement with respect to each other so that a surgeon may move the expanded retractor laterally to enlarge or maintain a surgical cavity in which it is located; and material covering the elongated members.

8. A laparoscopic medical device comprising in combination:

a cylindrical linear support means having a distal end and a proximal end;

a plurality of elongated members having distal ends and having proximal ends coupled adjacent to the distal end of the support means, each elongated member having a plurality of hinge points to facilitate lateral movement whereby relative axial movement between the support means and elongated members will cause the elongated members to move between a contracted configuration and an expanded planar configuration, with all of the elongated members located in a common plane with the axis of the support means, the total diameter of the contracted elongated members and support means being less than 1.5 centimeters; and a member of material with an interior opening receiving the elongated members for moving between a contracted and expanded configuration with the elongated means.

9. The device as set forth in claim 8 and further including a supplemental tube receiving the support means, elongated members and member of material.

10. A laparoscopic medical retractor for separating body parts during a surgical procedure to thereby create or maintain a surgical cavity comprising:

an interior rod having a distal end and a proximal end;

an exterior tube positioned to receive the interior rod, the exterior tube having a distal end and a proximal end;

a plurality of straps having their distal ends coupled to the distal end of the interior rod and having their proximal ends coupled in association with the distal end of the exterior tube, the straps having pivot points adjacent to their ends, the straps being flexible whereby movement of the distal end of the interior rod proximally toward the distal end of the exterior tube will cause the straps to assume an operative configuration, the total diameter of the retracted device being less than 1.5 centimeters;

coupling means to secure the interior rod and exterior tube against relative axial movement with respect to each other so that a surgeon may move the expanded retractor to enlarge a surgical cavity in which it is located; and material means covering the straps.

11. A laparoscopic medical retractor for separating body parts during a surgical procedure to thereby create or maintain a surgical cavity comprising:

an interior rod having a distal end and a proximal end;

an exterior tube positioned to receive the interior rod, the exterior tube having a distal end and a proximal end;

a plurality of straps having their distal ends coupled to the distal end of the interior rod and having their proximal ends coupled in association with the distal end of the exterior tube, the straps being formed with an interior component and exterior component bonded along their lengths, the straps being flexible whereby movement of the distal end of the interior rod proximally toward the distal end of the exterior tube will cause the straps to assume an operative configuration, the total diameter of the retracted device being less than 1.5 centimeters;

coupling means to secure the interior rod and exterior tube against relative axial movement with respect to each other so that a surgeon may move the expanded retractor to enlarge a surgical cavity in which it is located; and material covering the plurality of straps.

12. A laparoscopic medical retractor positionable in a supporting tube for separating body parts during a surgical procedure to thereby create or maintain a surgical cavity comprising:

an interior rod having a distal end and a proximal end;

an exterior tube positioned to receive the interior rod, the exterior tube having a distal end and a proximal end;

a plurality of straps having their distal ends coupled to the distal end of the interior rod and having their proximal ends coupled in association with the distal end of the exterior tube, the straps being formed with an interior component and exterior component bonded along their lengths, the straps being flexible whereby movement of the distal end of the interior rod proximally toward the distal end of the exterior tube will cause the straps to assume an expanded configuration with the total diameter of the retracted device being less than 1.5 centimeters; and coupling means to secure the interior rod and exterior tube against relative axial movement with respect to each other so that a surgeon may move the expanded retractor to enlarge a surgical cavity in which it is located.

13. The retractor asset forth in claim 12 and further including material means over the plurality of straps.

* * * * *